United States Patent [19]

Brown et al.

[11] Patent Number: 5,540,079
[45] Date of Patent: Jul. 30, 1996

[54] MICROWAVE EXCITED PHOTOACOUSTIC EFFECT CARBON MONITOR

[75] Inventors: Robert C. Brown, Ames; Jeffrey R. Dykstra, Churdan, both of Iowa

[73] Assignee: Iowa State University Research Foundation, Inc., Ames, Iowa

[21] Appl. No.: 298,115

[22] Filed: Aug. 30, 1994

[51] Int. Cl.$^6$ ............................................. G04N 7/00
[52] U.S. Cl. ..................... 73/23.33; 324/637; 73/24.01
[58] Field of Search ............................ 73/23.31, 23.33, 73/24.03, 587, 24.01; 324/637

[56] References Cited

U.S. PATENT DOCUMENTS

| | | | |
|---|---|---|---|
| 4,705,409 | 11/1987 | Trerice | 374/45 |
| 4,899,671 | 2/1990 | Bass | 374/122 |
| 5,060,507 | 10/1991 | Urmson et al. | 73/24.01 |
| 5,069,551 | 12/1991 | Brown | 356/432 |
| 5,112,215 | 5/1992 | Frish et al. | 431/3 |
| 5,299,692 | 4/1994 | Nelson et al. | 209/2 |
| 5,369,369 | 11/1994 | Cutmore | 324/637 |

OTHER PUBLICATIONS

R. C. Brown et al., "On–Line Determination of Unburned Carbon in Airborne Fly Ash", *Journal of Engineering for Gas Turbines and Power*, 112, 597–601 (Oct. 1990).
"Carbon–In–Ash Monitors", *EPRI M&D Center Technology Review*, 1–15 (Feb. 1994).
T. D'Annunzio, Brochure entitled "Microwave–based Carbon–In–Ash Monitoring System Demonstrated at Eddystone", *EPRI Innovators with EPRI Technology*, Electric Power Research Institute, Inc. (Dec. 1993).
G. Diebold et al., "Observation of the optoacoustic effect in the microwave region", *Applied Physics Letters*, 29, 447–449 (Oct. 1, 1976).
A. M. DiGioia, Jr., et al., "Reducing Power Generation Costs Via On–Line Measurement and Reduction of Carbon in Fly Ash", presented at the Southeastern Electric Exchange Meeting, Bal Harbour, FL, pp. 1–16 (Jun. 3, 1988).
J. Dykstra et al., "On–Line Monitoring of Carbon Loadings in Fluidized–Bed Fly Ash", *11th Annual Conference of Fluidized Bed Combustion*, pp. 7–12, Quebec, Canada (Apr. 1991).
F. R. Faxvog et al., "Carbon aerosol visibility vs. particle size distribution", *Applied Optics*, 17, 2612–2616 (Aug. 15, 1978).
P. G. W. Hawksley et al. in *Measurement of Solids in Flue Gases (Second Edition)*; P. G. W. Hawksley, Ed.; The Institute of Fuel: London (1977)—enclosed are the Title page, Copyright Page, and Table of Contents (pp. vi–vii).
*Noise Control in Industry*; J. D. Webb, Ed.; Sound Research Laboratories Limited: Suffolk, England (1976)—enclosed are the Title page, Copyright Page, and Table of Contents (pp. v–viii).
*Optoacoustic Spectroscopy and Detection*; Y–H. Pao, Ed.; Academic Press, Inc.: New York (1977)—enclosed are the Title Page, Copyright Page, and Table of Contents (pp. v–vi).
D. M. Roessler et al., "Optoacoustic measurement of optical absorption in acetylene smoke", *J. Opt. Soc. Am.*, 69, 1699–1704 (Dec. 1979).
A. Rosencwaig in *Photoacoustics and Photoacoustic Spectroscopy*; John Wiley & Sons: New York (1980)—enclosed are the Title page, Copyright Page, and Table of Contents (pp. vii–xii).
B. D. Sowerby et al., "On–Line Analysis in Coal–Fired Power Stations", presented at the Ninth International Conference on Coal Research, Washington DC, 9 pages (Oct. 13–16, 1991).
"Standard Test Method for Ash in the Analysis Sample of Coal and Coke from Coal", *Annual Book of ASTM Standards*, 5.05, Designation D3174–89, pp. 302–304 (1989).

Primary Examiner—Richard Chilcot
Assistant Examiner—Max Noori
Attorney, Agent, or Firm—Mueting, Raasch, Gebhardt & Schwappach, P.A.

[57] ABSTRACT

A method and apparatus for directing modulated microwave radiation at fly ash which absorbs the microwave energy and, in turn, emits minute acoustical waves. Those acoustic waves are measured by a microphone to determine the carbon content of the fly ash.

22 Claims, 3 Drawing Sheets

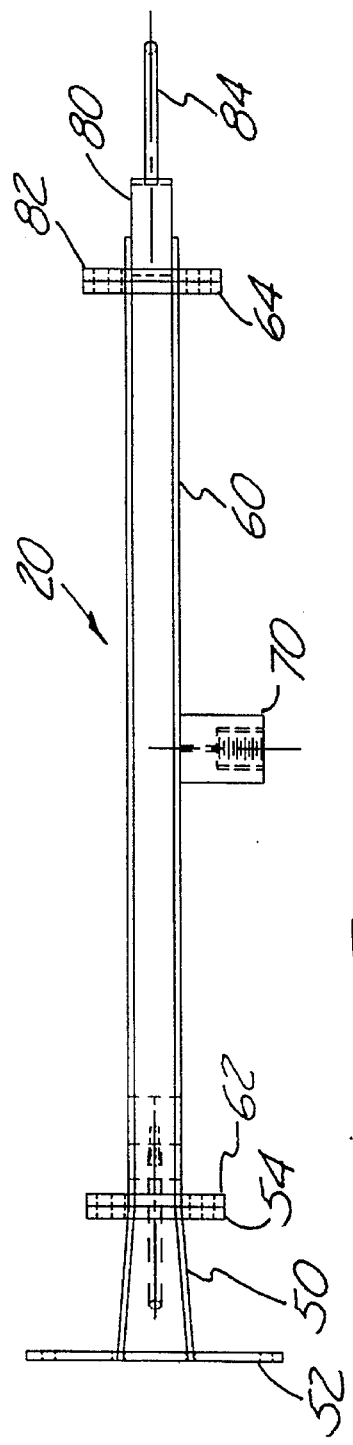
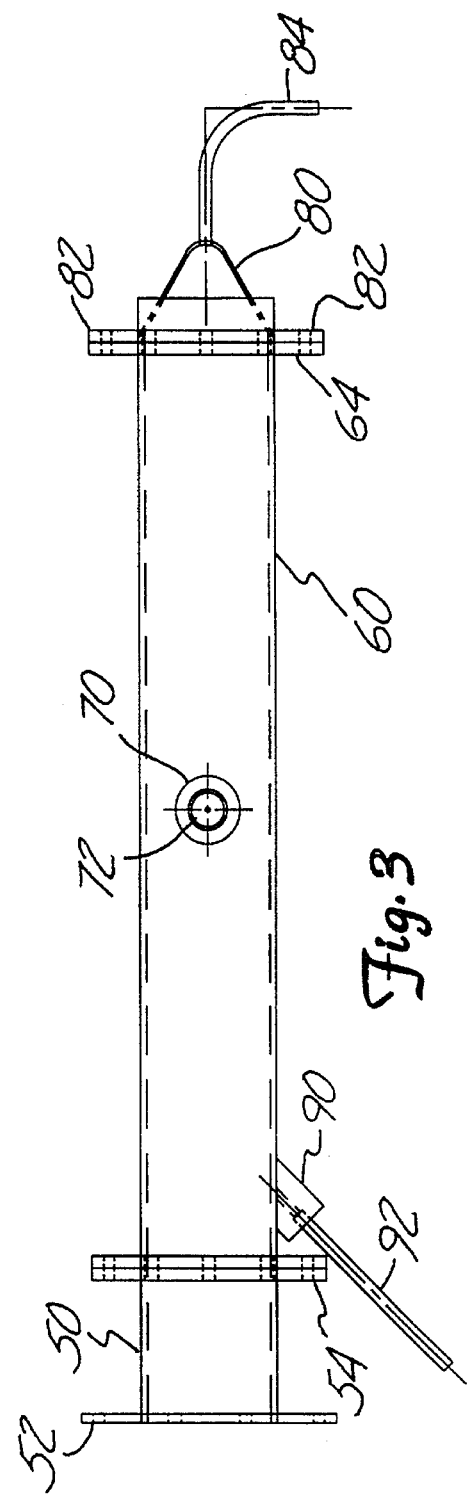

MICROWAVE EXCITED PHOTOACOUSTIC EFFECT CARBON MONITOR

STATEMENT OF U.S. GOVERNMENT RIGHTS

The U.S. Government has certain rights in this invention. This invention was made with U.S. Government grant support under DOC Grant No. ITA 87-02.

FIELD OF THE INVENTION

The present invention relates to the field of flue gas carbon monitoring. More particularly, the present invention relates to a method and apparatus for monitoring the level of carbon in fly ash based on the photoacoustic effect excited by microwave radiation.

BACKGROUND OF THE INVENTION

The carbon content of fly ash is the major determinant of combustion efficiency for coal-fire, d boilers. Carbon content is presently measured offline by a Loss-On-Ignition CLOI) test. The LOI test is typically performed by collecting a sample of fly ash from the boiler, weighing the sample, heating the sample to a temperature sufficient to drive moisture from the sample, reweighing the sample to determine the moisture content in the sample when collected, reheating the sample in an air stream to a temperature sufficient to oxidize the carbon in the sample to carbon dioxide, and weighing the remaining sample to determine the carbon content by the difference in weight between the sample prior to oxidation of the carbon and after the oxidation step.

There are a number of disadvantages associated with the typical LOI test. One disadvantage is the tedious and time consuming steps necessary to treat the sample to provide the relevant dam. Furthermore, the LOI test may introduce inaccuracies into the data if mineral matter, such as limestone or other substances, are present which exhibit weight changes upon heating in addition to the changes caused by carbon oxidation.

Attempts have been made to provide monitors based on the photoacoustic effects which occur when energy is directed at the fly ash in the flue gas of a coal-fired furnace. Briefly, the photoacoustic effect is caused by the absorption of energy by the carbon in the fly ash. After absorbing-energy, the carbon produces a thermal wave which, in turn, produces a minute acoustical signal generated at a frequency equal to the modulation frequency of the energy Previous attempts at producing carbon monitors based on the photoacoustic effect employed optical energy as the excitation source. The disadvantage with such systems is, however, that the response is typically dependent upon the size distribution of the carbon particles in the sample unless the wavelength of the excitation radiation is much larger than the largest particle in the sample being tested. Fly ash typically includes carbon particles ranging in size from 10 microns to 100 microns in diameter. Optical radiation, however, typically has a wavelength of less than 0.7 μm. As a result, the photoacoustic response of fly ash samples to laser radiation excitation is typically dependent upon the size of the carbon particles in the sample.

SUMMARY OF THE INVENTION

The present invention includes a method and apparatus by which modulated microwave radiation is directed at fly ash which absorbs the microwave energy and, in turn, emits minute acoustical waves. Those acoustic waves are measured by a microphone to determine the carbon content of the fly ash.

One advantage of the present invention is that the microwave region of the electromagnetic spectrum includes radiation with wavelengths of 5 mm or more which is sufficiently large to assure that the photoacoustic signal generated by the microwave radiation is independent of the particle size distribution in the fly ash sample.

Another advantage of the present invention is that the fly ash can be tested on-line by sampling the flue gas as it is produced, thereby providing information regarding the carbon content of fly ash quickly and efficiently.

Various other features and advantages of the present invention will be apparent upon a reading of the detailed description below along with reference to the drawings, which form a part hereof.

BRIEF DESCRIPTION OF THE DRAWINGS

FIG. 2 is a top view of one preferred photoacoustic chamber for use in connection with the present invention.

FIG. 3 is a side view of the photoacoustic chamber of FIG. 2.

DETAILED DESCRIPTION OF THE INVENTION

Figure 1:
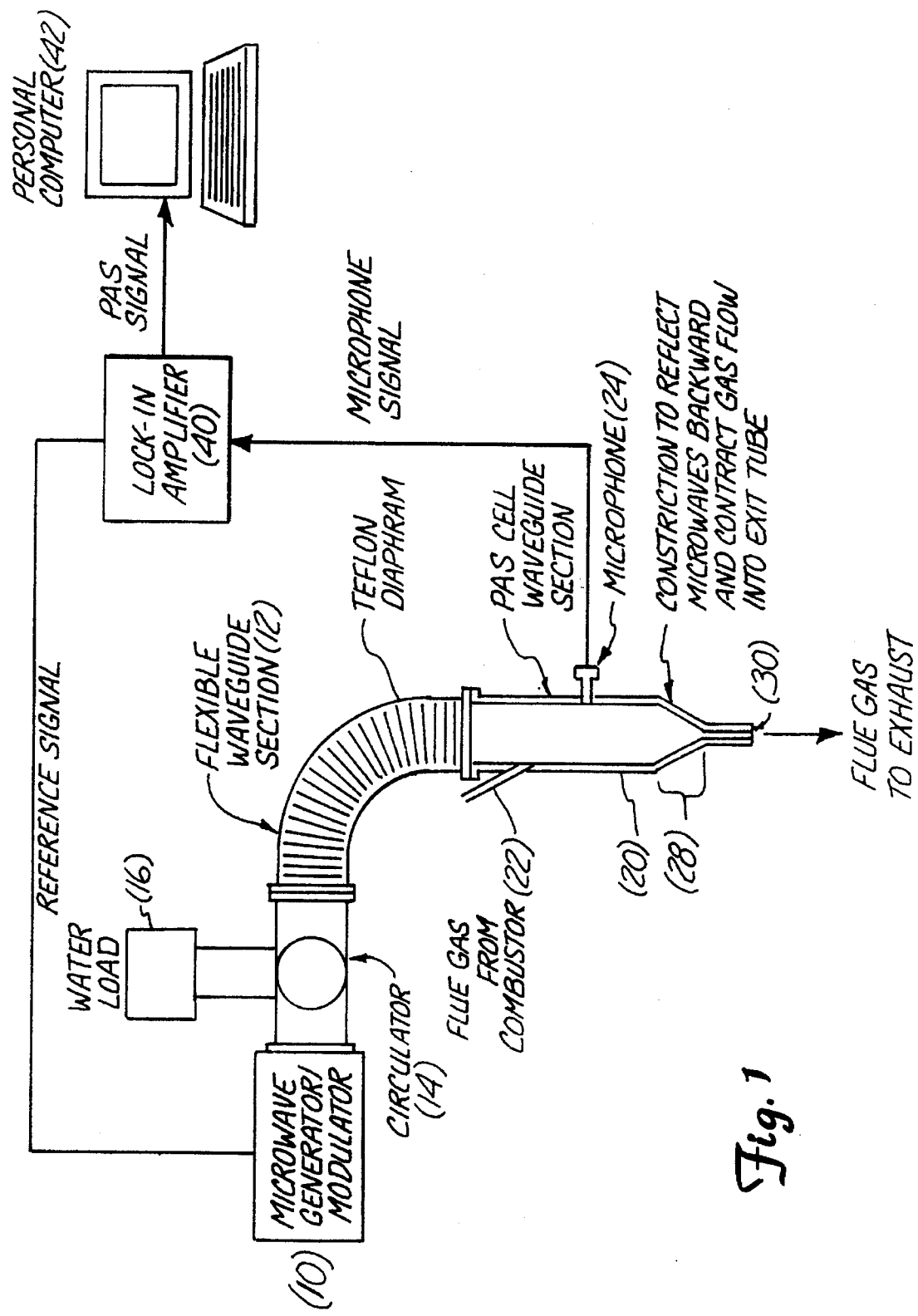
FIG. 1 is a schematic diagram of a system according to the present invention.

FIG. 1 depicts a schematic diagram of a system according to the present invention. The system includes a microwave generator/modulator 10 which directs microwave energy to the flexible wave guide section 12. Wave guide section 12 opens into photoacoustic chamber 20.

Flue gas from the combustion source is introduced directly into photoacoustic chamber 20 through tube 22 which enters photoacoustic chamber at an angle oblique to its longitudinal axis. A microphone 24 is provided in communication with the interior of the photoacoustic chamber 20 to detect the acoustic signal generated by the system.

An exit port 30 is provided at the lower end of the photoacoustic chamber 20 to exhaust the flue gas and entrained fly ash introduced into the chamber 20 through tube 22.

The preferred photoacoustic chamber 20 is constricted towards the exhaust port 30 to reflect microwaves back towards the waveguide 12. The reflected microwave radiation is intercepted by circulator 14 before it can impinge on the microwave generator 10. The circulator 14 redirects the reflected microwave radiation towards water load 16 to protect the microwave generator. Microphone 24 is connected to the lock-in amplifier 40 which is also connected to receive a reference signal from the microwave generator. The lock-in amplifier 40 generates a signal corresponding to the carbon mass loading of the fly ash entrained in the flue gas which can then be used to determine the efficiency of the combustion source which is the source of the flue gas.

The preferred microwave generator 10 produces microwave radiation with a wavelength of 120 mm, although microwave energy with wavelengths ranging from about 1 mm to about 120 mm could be used. The preferred generator 10 is a conventional magnetron device similar to those used in domestic microwave ovens.

The microwave generator 10 is, however, modified to modulate its output by switching the electric current to the magnetron on and off. The switching is preferably at a frequency of about 1 kHz and in the present invention is accomplished by a high power vacuum switch, although it would be understood that many other switching technologies such as solid state switching controls could be used in place of the vacuum robe switch. Although the preferred frequency for modulation is 1 klk a preferred range lies between about 200 Hz to about 2 kHz.

As a result of the modulation, microwave radiation is generated as a rectangular wave and directed into the wave guide 12. A reference signal of the microwave radiation (as a rectangular wave) is provided to the lock-in amplifier 40 for comparison to the signal generated by microphone 24.

The lock-in amplifier 40 is used to identify and separate signals from the microphone 24 from background noise by discriminating signals of a known frequency, i.e., the microwave generator 10, from within the wider frequency spectrum of the background noise. In the preferred embodiment, the signal identified by the lock-in amplifier 40 is preferably stored on a computer attached to the lock-in amplifier 40. As a result, data collected by the system can be stored, retrieved and otherwise, manipulated to facilitate analysis.

One preferred chamber 20 is shown in greater detail in FIGS. 2 and 3. In general, the photoacoustic chamber 20 has a rectangular cross section. FIG. 2 is a view orthogonal to the narrow side of the rectangular cross section of the photoacoustic chamber 20.

The preferred chamber 20 is constructed of three sections connected by flanges. The center section 60 includes flanges 62 and 64 at opposing ends. Flange 62 is connected to flange 54 of transition section 50 which includes flange 52 which is attached to the flexible wave guide section 12 as shown in FIG. 1. A teflon gasket (not shown) is provided between flanges 54 and 62 to physically separate the center section 60 of chamber 20 from the remainder of the wave guide 12, while permitting microwave energy to enter the chamber from wave guide 12.

In the preferred embodiment, the transition section 50 reduces the shortest dimension (cell height) of the rectangular cross section of chamber 20 from 3.3 centimeters to 2.1 centimeters. This dimension is not critical to the propagation of microwave energy through the wave guide 12, but it does determine the electromagnetic field intensity of the microwave energy in the chamber 20 as well as the flow velocity of the flue gas and density of the fly ash in center section 60. It would be preferred to have an even smaller dimension for the cell height of center section 60 of chamber 20, but the cell height of chamber 20 must be balanced against the field intensity which can become large enough to produce undesirable sparking between the other two sides of chamber 20.

The dimensions of the other two sides (cell width) of center section 60 of chamber 20 preferably equal one-half the wavelength of the microwave radiation used to excite the fly ash.

In the preferred embodiment, the length of center section 60 of chamber 20 is 48.3 centimeters. The length of center section 60 is not critical although the amount of microwave energy absorbed increases with the center section 60 length. The increase in absorption must, however, be balanced against a corresponding decrease in intensity of the acoustical signal generated by the absorption.

Center section 60 also includes fitting 70 preferably attached to the wider side of chamber 20. In FIG. 3, it can be seen that fitting 70 includes a bore 72 which is preferably threaded and further includes an inner bore 74 which opens into center section 60. Inner bore 74 has a diameter which preferably does not exceed about 3.2 millimeters (⅛ inch). Microphone 24 is threaded into bore 72 in fitting 70 and, thus, can receive acoustic signals generated by absorption of the energy in the carbon portion of the fly ash within center section 60. Fitting 70 is preferably constructed of brass, although ninny other materials could be used in lieu of the preferred brass.

Placement of fixture 70 is preferably approximately midpoint along center section 60, although other locations could be substituted. The location of fitting 70 should be downstream from the entry point of flue gas into chamber 20.

Center section 60 also includes fitting 90 from which tube 92 extends. Fitting 90 includes a bore which enters the cavity formed in center section 60. Tube 92 and the bore in fitting 90 preferably enter center section 60 at an oblique angle which, in the preferred embodiment is 45 degrees off of the longitudinal axis through center section 60.

Tube 92 and fitting 90 are used to introduce flue gas into center section 60. As such, it is helpful to provide tube 92 and fitting 90 at an oblique angle to facilitate flow of the flue gas through center section 60 and towards exit section 80 which is more fully described below.

Tube 92 and fitting 90 are preferably constructed of brass to prevent their deterioration from the microwave energy introduced into chamber 20. Brass tube 92 should have a length of at least about 7.6 centimeters to prevent leakage of the microwave energy from chamber 20. Beyond the length of tube 92, robing of any material can be connected without concern for deterioration from the microwave energy introduced into chamber 20.

At the end of center section 60 opposite transition section 50, exit section 80 is ached to center section 60 through the use of flange 82 which mates with flange 64. Exit section 80 includes tube 84 which carries away the flue gas introduced into chamber 20.

Exit section 80 tapers from a wide rectangular cross section similar to that provided in center section 60 to an exit bore into which tube 84 is inserted. In the preferred embodiment, robing 84 has a 6.4 mm (¼ inch) OD.

The taper in exit section 80 serves two purposes. It funnels the particulate laden flue gas out of chamber 20 while accelerating the gas flow due to the reduced cross sectional area. Acceleration of the gas flow facilitates removal of particles which may otherwise settle at the end of chamber 20. In the preferred embodiment, the tapering sides of exit section 80 form an angle of 30° with the longitudinal axis of center section 60.

A second purpose served by the tapering of exit section 80 is to reflect microwave energy back through the chamber 20, wave guide 12, and into circulator 14 where the reflected energy is diverted off into water load 16.

If desired, the entire photoacoustic chamber 20 may be heated and insulated to maintain the flue gas above its acid dewpoint. This will ensure that data collected in photoacoustic chamber 20 is accurate as the microwave energy will primarily be absorbed by the carbon portion of the fly ash. If chamber 20 is heated, the brass fixture 70 for microphone 24 can be air or water cooled, if necessary, to maintain microphone 24 below its maximum recommended operating temperature.

Figure 4:
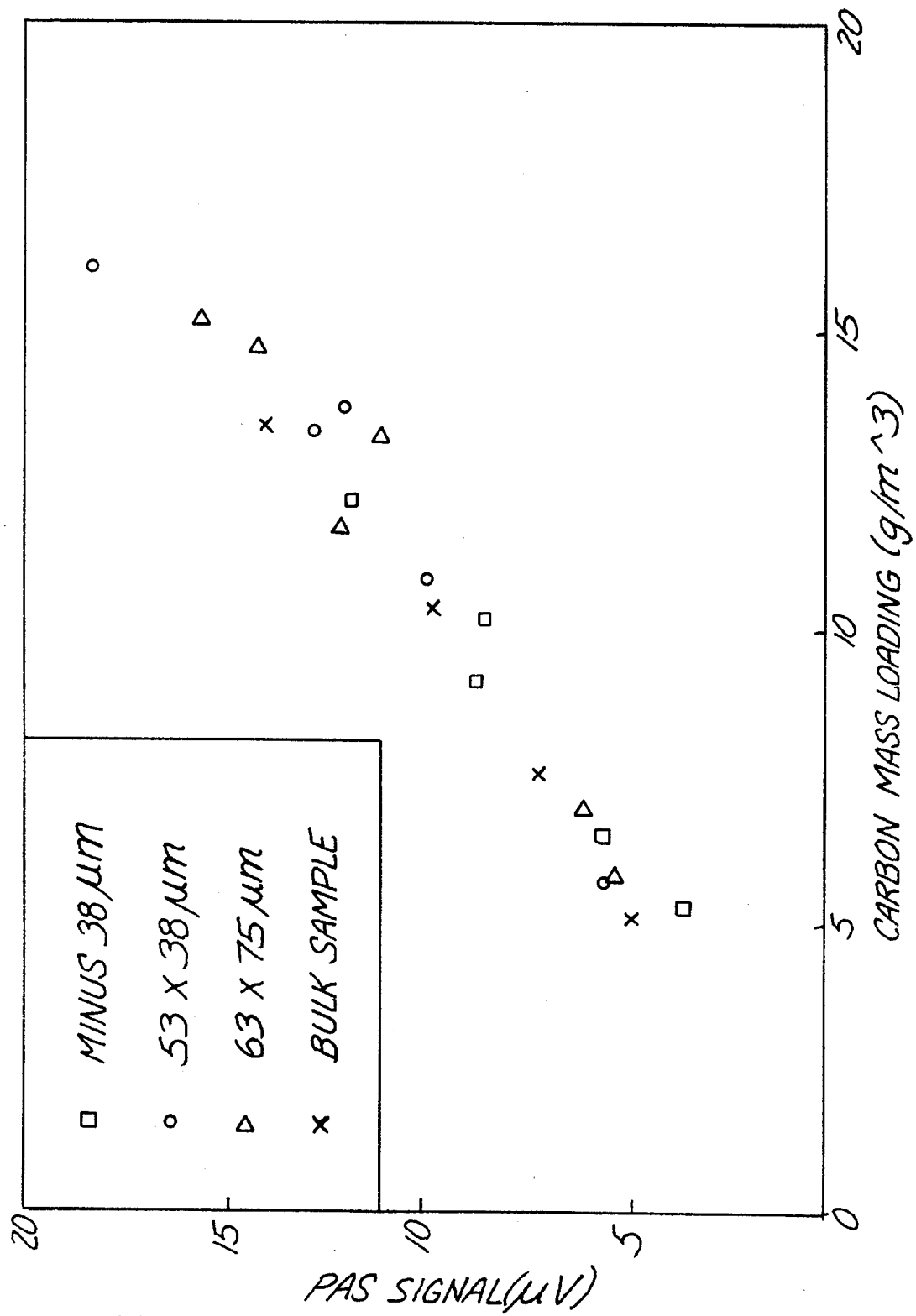
FIG. 4 is a graph depicting experimental data collected using a system according to the present invention.

Referring now to FIG. 4, a graph depicting the results of tests conducted using the apparatus and method according to the present invention are depicted. To provide useful data, the system preferably provides a signal which is linear with the carbon content entrained in the fly ash and which is also independent of the particle size distribution of the fly ash. To determine linearity of the apparatus and method, a large sample of stoker boiler fly ash was obtained and separated into portions with known particle size distributions. -One sample of fly ash consisted of particles that were smaller than 38 microns in diameter. A second portion of the sample was separated into particles having a size of 38 to 53 microns with a median size of 46 microns. A third portion of the fly ash was separated into particles having a size in the range of 63 to 75 microns with a median size of 69 microns in diameter. Finally, a sample of bulk fly ash was also tested to establish that the signal was linear with the carbon content of the fly ash and independent of the particle sizes in the samples.

Each of the samples were entrained in an air stream and introduced into the photoacoustic chamber 20 through a tube 92 as depicted in FIGS. 1 through 3 to simulate a flue gas delivery method. Microwave energy was directed into the photoacoustic chamber 20 and the resulting signal was measured in microvolts as shown in FIG. 4.

The results indicate that the system and method according to the present invention do provide a signal which is essentially linear with the carbon content in each sample and is also independent of the particle size distribution of the fly ash being tested.

Although the microwave generator 10 of the preferred system produces energy having a wavelength of 120 millimeters, it will be understood that microwave energy having other wavelengths can also be used provided the wavelengths are significantly longer than the diameter of the fly ash particles. Shorter wavelengths of microwave energy can, in fact, increase the sensitivity of the system due to increased absorptivity of the carbon particles in the fly ash. That increased sensitivity must, however, be balanced with the next to maintain a wavelength long enough to provide a signal which is independent of the particle size distribution of the fly ash being tested. It is preferred that the microwave energy have a wavelength of at least about ten times the diameter of the largest particle size typically found in the fly ash to be measured.

As an alterative to the invention described above, in which fly ash is introduced into photoacoustic chamber 20 as a component of the flue gas, the fly ash can be moved through a photoacoustic chamber and tested as a bulk solid as opposed to a gas entrained particle system.

One advantage of a bulk solid system is the increased concentration of carbon particles in the acoustic chamber which facilitates detection of carbon at low weight fractions.

In one embodiment, a system for testing fly ash as a bulk solid could include directing a flue gas through a separator, such as a cyclone, to separate the fly ash from the flue gas. As the fly ash particles drop from the separator, they would be directed by gravity through the photoacoustic chamber, forming a stream of flowing powder which moves through the acoustic chamber.

A disadvantage to the bulk solid approach is that the advantage obtained by the response of online monitoring of the flue gas is compromised by the amount of lag time necessary to move the bulk powder through the photoacoustic chamber.

While the present invention has been described above, it will be understood that many modifications may be readily made and that this application is intended to cover any adaptations or variations of the system and method as described above. Therefore, it is intended that this invention be limited only by the claims and equivalences thereof.

We claim:

1. A system for measuring carbon content in fly ash comprising:

a) a chamber;

b) an opening into the chamber, the opening allowing the introduction of fly ash into the chamber;

c) a microwave energy source directing modulated microwave energy into the chamber, at least a portion of the microwave energy being absorbed by carbon in the fly ash; and d) a detector connected to the chamber, the detector for detecting acoustic energy produced by the absorption of the microwave energy by the carbon in the chamber.

2. A system according to claim 1, wherein the opening into the chamber is in communication with a coal-fired furnace.

3. A system according to claim 1, wherein the microwave energy has a wavelength of about 1 mm to about 120 mm.

4. A system according to claim 1, wherein the microwave energy has a wavelength of about at least 10 times that of the largest particle size of the fly ash introduced into the chamber.

5. A system according to claim 1, wherein the microwave energy is modulated to a frequency of about 1 kHz.

6. A system according to claim 1, wherein the microwave energy is modulated to a frequency of about 200 Hz to about 2 kHz.

7. A system according to claim 1, wherein the detector comprises a microphone.

8. A system according to claim 1, further comprising means for identifying acoustic energy produced by the absorption of microwave energy by carbon in the fly ash introduced into the chamber.

9. A system for measuring carbon content in fly ash comprising:

a) a chamber;

b) an opening into the chamber, the opening being in communication with a coal-fired furnace and allowing the introduction of fly ash into the chamber;

c) a microwave energy source directing microwave energy into the chamber, wherein the microwave energy has a wavelength of about at least 10 times that of the largest particle size of the fly ash introduced into the chamber, and further wherein at least a portion of the microwave energy is absorbed by carbon in the fly ash; and d) a detector connected to the chamber, the detector comprising a microphone for detecting acoustic energy produced by the absorption of the microwave energy by the carbon in the chamber.

10. A method of determining the carbon content of fly ash from a coal-fired furnace, the method comprising the steps of:

(a) introducing fly ash into a chamber;

(b) directing modulated microwave energy into the chamber so that carbon in the fly ash absorbs at least a portion of the microwave energy; and (c) detecting acoustic energy produced by the energy absorbed by the carbon in the fly ash.

11. A method according to claim 10, wherein the step of introducing fly ash further comprises directing at least a portion of flue gas from the furnace directly into the chamber, the flue gas entraining the fly ash.

12. A method according to claim 10, wherein the step of introducing fly ash further comprises extracting fly ash from the flue gas and introducing the extracted fly ash into the chamber.

13. A method according to claim 10, further comprising the step of maintaining the temperature of the chamber above an acid dewpoint of the flue gas.

14. A method according to claim 10, wherein the step of directing microwave energy further comprises providing the microwave energy with a wavelength of about 1 mm to about 120 mm.

15. A method according to claim 10, wherein the step of directing microwave energy further comprises providing the microwave energy with a wavelength of about 10 times that of the largest particle size of the fly ash introduced into the chamber.

16. A method according to claim 10, wherein the step of directing microwave energy further comprises modulating the microwave energy to a frequency of about 1 kHz.

17. A method according to claim 10, wherein the step of directing microwave energy further comprises modulating the microwave energy to a frequency of about 200 Hz to about 2 kHz.

18. A method according to claim 10, wherein the step of detecting energy further comprises detecting acoustic energy produced by absorption of the microwave energy and resulting heating of the carbon in the fly ash.

19. A method according to claim 10, further comprising the step of identifying acoustic energy produced by absorption of the microwave energy and resulting heating of the carbon in the fly ash.

20. A method according to claim 19, wherein the step of identifying further comprises the steps of:

1) generating a fast signal corresponding to the microwave energy;

2) generating a second signal corresponding to acoustic energy in the chamber; and 3) comparing the-fast and second signals to identify the acoustic energy produced by absorption of the microwave energy and resulting heating of the carbon in the fly ash.

21. A method of determining the carbon content of fly ash from a coal-fired furnace, the method comprising the steps of:

a) introducing fly ash into a chamber;

b) directing microwave energy into the chamber so that carbon in the fly ash absorbs at least a portion of the microwave energy, wherein the microwave energy has a wavelength of about 1 mm to about 120 mm, and further wherein the microwave energy is modulated to a frequency of about 200 Hz to about 2 kHz; and c) detecting acoustic energy produced by absorption of the microwave energy and resulting heating of the carbon in the fly ash; and d) identifying acoustic energy produced by absorption of the microwave energy and resulting heating of the carbon in the fly ash.

22. A method according to claim 21, wherein the step of identifying further comprises the steps of:

1) generating a fast signal corresponding to the microwave energy;

2) generating a second signal corresponding to acoustic energy in the chamber; and 3) comparing the first and second signals to identify the acoustic energy produced by absorption of the microwave energy and resulting heating of the carbon in the fly ash.

* * * * *

UNITED STATES PATENT AND TRADEMARK OFFICE
CERTIFICATE OF CORRECTION

PATENT NO.: 5,540,079
DATED: July 30, 1996
INVENTOR(S): Robert C. Brown and Jeffrey R. Dykstra It is certified that error appears in the above-identified patent and that said Letters Patent is hereby corrected as shown below:

Col. 1, line 36, delete "dam" and insert --data--
Col. 1, line 48, delete "energy" and insert --energy source.--
Col. 3, line 8, delete "robe" and insert --tube--
Col. 3, line 9, delete "klk" and insert --kHz,--
Col. 4, line 9, delete "ninny" and insert --many--
Col. 4, line 32, delete "robing" and insert --tubing--
Col. 4, line 36, delete "ached" and insert --attached--
Col. 4, line 44, delete "robing" and insert --tubing--
Col. 8, line 3, delete "the-fast" and insert --the first--
Col 8, line 26, delete "fast" and insert --first--

Signed and Sealed this

Twenty-fifth Day of November, 1997

Attest:

BRUCE LEHMAN

Attesting Officer

Commissioner of Patents and Trademarks